(12) United States Patent
Mouchawar et al.

(10) Patent No.: US 6,847,843 B1
(45) Date of Patent: Jan. 25, 2005

(54) METHOD AND APPARATUS FOR ELECTROPHYSIOLOGICAL TESTING IN AN IMPLANTABLE DEVICE

(75) Inventors: Elia Arambula Mouchawar, Newhall, CA (US); Bonian Dai, Temple City, CA (US); Mohssen Fard, Woodland Hills, CA (US); Gregory Hauck, Valencia, CA (US); Corey L. Brown, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 423 days.

(21) Appl. No.: 09/876,755

(22) Filed: Jun. 6, 2001

(51) Int. Cl.$^7$ ................................................ A61N 1/18
(52) U.S. Cl. ................................ 607/27; 607/30
(58) Field of Search ...................... 607/27–28, 30–32, 607/60; 600/510

(56) References Cited

U.S. PATENT DOCUMENTS

| | | | |
|---|---|---|---|
| 4,419,996 A | 12/1983 | Tarjan | 128/419 PG |
| 4,515,160 A | 5/1985 | Keimel | 128/419 PG |
| 5,277,190 A | 1/1994 | Moulton | 128/705 |
| 5,466,254 A | 11/1995 | Helland | 607/123 |
| 5,653,737 A | 8/1997 | van Lake | 607/9 |
| 5,709,711 A | 1/1998 | Fain | 607/8 |
| 5,735,880 A | 4/1998 | Prutchi et al. | 607/9 |
| 5,925,067 A | 7/1999 | Lu | 607/28 |
| 5,928,271 A | 7/1999 | Hess et al. | 607/14 |
| 5,974,341 A | 10/1999 | Er et al. | 607/31 |

*Primary Examiner*—Mark Bockelman

(57) ABSTRACT

An implantable cardiac stimulation device and associated method capable of delivering non-invasive programmed stimulation for electrophysiological testing in which the onset of the non-invasive programmed stimulation is triggered by a cardiac event, either a detected intrinsic event or a stimulated event, occurring in the heart chamber to be tested. When a non-invasive programmed stimulation command is received by the implanted device, it switches to a routine that allows transition to a non-invasive programmed stimulation from a standard operating mode, during a refractory period. The stimulation device also provides a recovery delay following the last pulse of a non-invasive programmed stimulation sequence. If no intrinsic activity is detected during the recovery delay, a refractory period is started following the expiration of the recovery delay. During this refractory period, a transition from the non-invasive programmed stimulation state machine back to the standard stimulation state machine is accomplished.

19 Claims, 10 Drawing Sheets

METHOD AND APPARATUS FOR ELECTROPHYSIOLOGICAL TESTING IN AN IMPLANTABLE DEVICE

FIELD OF THE INVENTION

The present invention relates to the general field of implantable cardiac devices, and particularly to an apparatus and associated method for performing non-invasive synchronized electrophysiological ("EP") testing in an implantable cardioverter-defibrillator. More specifically, the present invention is directly related to an implantable cardiac stimulation device capable of delivering non-invasive programmed stimulation for electrophysiological testing in which the onset of the non-invasive programmed stimulation is triggered by a cardiac event occurring in a heart chamber to be tested, whereupon software controls within the implanted device execute a transfer between stimulation state machines.

BACKGROUND OF THE INVENTION

Implantable cardioverter-defibrillators, commonly known as ICDs, are cardiac stimulation devices that detect and treat various cardiac arrhythmias including bradycardia (too slow of a heart rate), tachycardia (too fast of a heart rate) and fibrillation. Usually implanted in the pectoral region, an ICD is typically coupled to a patient's heart through transvenous leads that are used to sense electrical signals from the heart and deliver both low voltage and high voltage electrical therapy to the heart to correct detected rhythm dysfunctions. A serious form of cardiac arrhythmia is ventricular fibrillation, which is often fatal if not treated shortly after it begins.

Electrophysiological ("EP") testing is a procedure that is commonly used to evaluate an individual's susceptibility to cardiac arrhythmias, particularly atrial and ventricular tachycardia. Electrophysiological testing is normally required during an ICD implant procedure and sometimes during follow-up clinical visits. During an electrophysiological study, the ability to induce and terminate tachycardia and/or fibrillation is tested by applying a sequence of high rate pulses, sometimes called "bursts," that are known to either induce or terminate an arrhythmia. By inducing tachycardia in a patient's heart, a determination can be made as to whether an implanted ICD is functioning properly in detecting and terminating the tachycardia and if its parameters have been optimally programmed.

Electrophysiological testing may include induction of fibrillation and delivery of shocks to determine the defibrillation threshold ("DFT") for the particular patient. This determination allows the physician to program the defibrillation shocks with an appropriate energy and safety margin. The physician is also able to determine if the selected ICD and implanted electrode configuration will be effective. The implanted electrode configuration may result in unacceptably high defibrillation threshold or the ICD may not have enough energy output to provide a safety margin (typically about 10 joules) over the determined defibrillation threshold. Electrophysiological testing also provides useful diagnostic information to be used by the physician in selecting the most effective tachycardia detection and cardioversion algorithms to be used by the ICD.

Electrophysiological testing, which can also be used to determine if a particular patient would respond favorably to other therapies such as drug therapies used to treat cardiac arrhythmias, has traditionally been an invasive procedure, requiring surgery to place electrodes in contact with desired locations in the patient's heart. Electrical leads couple the implanted electrodes with an external stimulation device capable of delivering bursts of stimulation for the induction of tachycardia as well as low-voltage and high-voltage therapies used to terminate tachycardia.

During an ICD implant procedure, electrophysiological testing can be performed using an external device for delivering electrical pulses to the patients heart by connecting electrical leads to the implanted leads positioned in the heart. A series of carefully timed, high-rate pulses or bursts can be delivered in order to overdrive pace the heart and to induce tachycardia or fibrillation. The external device can deliver cardioversion shocks or high voltage defibrillation shocks, substantially similar to those from an ICD, in order to terminate the induced arrhythmia. In this way, the physician can perform an electrophysiological evaluation of the patient and select the optimal values for parameters to be programmed in the implanted ICD.

However, in order to ease the implant procedure, it is desirable to have the testing functions of an external device incorporated directly into the ICD to eliminate the need for additional equipment. Furthermore, during follow-up office visits, non-invasive EP testing is strongly preferred in order to avoid risks commonly associated with any surgical procedure, such as bleeding, thrombosis or infection.

Non-invasive electrophysiological testing can be performed on patients who have received an implantable cardiac stimulating device such as a pacemaker or ICD. The implanted cardiac stimulation device can be used in a 'trigger' mode to track burst stimulation pulses delivered externally by an external stimulation device. The implanted cardiac stimulation device may also be used in an "inhibit" mode in which release of stimulation pulses is controlled by an external stimulation device and a programmer having telemetric communication with the implanted device.

Alternatively, a software or algorithm that is specifically designed for electrophysiological testing may be included in a pacemaker or ICD programmer, eliminating the need for a separate external stimulation device. The ICD programmer is used to send commands to the implanted device to cause administration of burst stimulation in a desired sequence to either induce or terminate an arrhythmia. This process may be referred to as non-invasive programmed stimulation or "NIPS." For additional details regarding an ICD possessing non-invasive electrophysiological testing capabilities reference is made to U.S. Pat. No. 5,709,711 to Fain, which is incorporated herein by reference.

Certain currently available ICDs have the capability for noninvasive induction and termination of arrhythmias to monitor and test the effectiveness of selected detection criteria and therapies. For example, an ICD may be slaved to an external laboratory stimulator to be used as a timing-signal source to allow signals communicated to the ICD via telemetry to be delivered to the patient with the same timing as the laboratory stimulator output. It also allows the ICD to deliver high-rate pulses through the defibrillation electrodes.

Another ICD provides certain electrophysiological testing capabilities including the ability to confirm the ability to induce the patient's clinical arrhythmia and evaluation of the effectiveness of various ICD therapies in termination of the clinical arrhythmia, when used in connection with an external programmer. While this approach provides certain desirable testing features, it would still be desirable to have full flexibility to allow the ICD to provide all of the functions of an external high voltage stimulator.

One problem with presently available systems is that they provide only limited control over the implanted pulse generator timing and operation. Normally, the pacing operations of the implanted pacemaker or ICD are first disabled in any heart chambers that are not being tested. This can be done by setting the pacing mode to a single-chamber pacing mode or by programming pacing parameters in other chambers to ineffective settings such as a sub-threshold pacing output.

Devices normally operating in a dual-chamber pacing mode are typically set to a single chamber mode during electrophysiological testing in order to prevent high-rate stimulation in one chamber (e.g. the atrium) from causing the other chamber (e.g. the ventricle) to follow the high rate activity. Otherwise, delivery of the high rate stimulation pulses in one chamber may be sensed in another chamber as intrinsic events leading to pacemaker-induced arrhythmia. Thus, pacing support in non-tested chambers is commonly withheld during electrophysiological testing.

Patients having conduction disorders, however, may require pacing support in other chambers during electrophysiological testing. For example, patients lacking atrial-ventricular (AV) conduction require ventricular pacing support during atrial electrophysiological testing. U.S. Pat. No. 5,653,737 to van Lake, which is incorporated herein by reference, describes a dual-chamber pacemaker in which the atrial and ventricular channels can operate simultaneously yet independently so that, during noninvasive electrophysiological testing for atrial tachycardias, the device can generate bursts of pacing pulses to induce and terminate atrial arrhythmias, while maintaining ventricular pacing support. In the '737 patent, the pacing mode is advantageously changed at the start of non-invasive programmed stimulation to an atrial pacing mode which allows burst stimulation for EP testing in the atrium and to an independent ventricular pacing mode which may be VOO, VVT, or preferably VVI, to allow pacing support in the ventricle.

A command from an external stimulator is conventionally used to initiate non-invasive programmed stimulation. Upon receipt of the external command, the pacing mode of the implanted device is changed to the pacing mode desired during the electrophysiological test, often a single-chamber triggered mode. The delivery of the first stimulation pulse of the non-invasive programmed stimulation sequence is triggered only by the external command, thus it is delivered asynchronously with the cardiac cycle.

It would therefore be desirable to include in an implantable cardiac stimulation device, capable of performing non-invasive electrophysiological testing, a method for safely and automatically transitioning from the standard operating mode to a non-invasive programmed stimulation mode in a way that is synchronized to the cardiac cycle. It is further desirable that the delivery of non-invasive programmed stimulation in one cardiac chamber is decoupled from stimulation and sensing occurring in other cardiac chambers. It is still further desirable to provide safe back-up stimulation support in ventricular heart chambers during atrial non-invasive programmed stimulation so that cardiac output can be maintained during the atrial testing. Cardiac synchronized transition back to the standard operating mode of the cardiac stimulation device is desirable at the end of the non-invasive programmed stimulation. Cardiac synchronized transition between non-invasive programmed stimulation and the standard stimulation mode improves device safety by avoiding undesirable asynchronous stimulation of the heart chambers.

SUMMARY OF THE INVENTION

The present invention addresses these problems by providing an implantable cardiac stimulation device capable of delivering non-invasive programmed stimulation for electrophysiological testing (an electrophysiological testing scheme) in which the onset of the non-invasive programmed stimulation is triggered by a cardiac event, either a detected intrinsic event or a stimulated event, occurring in the heart chamber to be tested. After receipt of an external command, software controls within the implanted device execute a transfer between stimulation state machines.

During the standard stimulation mode of the implanted device, hardware interrupts cause software controls to perform expected tasks, also referred to as "interrupt service routines." Such hardware interrupts are triggered by a detected P-wave or R-wave (intrinsic depolarizations occurring in the atrium or the ventricle, respectively) or an A-pulse or V-pulse (stimulation pulses delivered in the atrium or ventricle, respectively).

When a non-invasive programmed stimulation command is received by the implanted device, the software control responding to a hardware interrupt is switched to a routine that allows transition to a non-invasive programmed stimulation rather than continuing in the standard operating mode. Hence, this transition between a standard stimulation state machine and a non-invasive programmed stimulation state machine occurs during the refractory period that follows a triggering cardiac event. Thus, safe, cardiac-synchronized transition between state machines is accomplished.

The present invention also provides a recovery delay following the last pulse of a non-invasive programmed stimulation sequence. This recovery delay is allowed for the sinus node to recover its normal rhythm. If no intrinsic activity is detected during the recovery delay, a refractory period is started following the expiration of the recovery delay. If an intrinsic activity is detected during the recovery delay, the refractory period is started immediately after the sensed event. During this refractory phase, safe, synchronized transition from the non-invasive programmed stimulation state machine back to the standard stimulation state machine is accomplished.

By separating the control of the stimulation modes, the standard operating code is protected, as the code for non-invasive programmed stimulation is only executed following a non-invasive programmed stimulation command. Once the code for the non-invasive programmed stimulation is executed, built-in safety features allow the stimulation device to automatically transfer back to the standard stimulation state machine. These features are activated when entering the non-invasive programmed stimulation and in an unlikely event of code corruption in the non-invasive programmed stimulation state machine, there will be a transfer of control back to the standards simulation state machine.

In one embodiment, the present invention further provides decoupling of the device operation in tested and non-tested chambers of the heart. Stimulation and sensing of heart chambers not being tested is decoupled from stimulation in the heart chamber undergoing non-invasive programmed stimulation. Stimulation pulses delivered in the tested chamber may be wrongly detected as intrinsic events in other heart chambers. Such misdetection can lead to pacemaker-induced arrhythmias because inhibition of pacing pulses may occur when pacing is actually needed. The present invention overcomes this problem by providing blanking of the sensing circuitry of non-tested heart chambers during delivery of stimulation pulses in the tested chamber.

The present invention further provides back-up ventricular pacing whenever atrial non-invasive programmed stimulation is performed. Back-up ventricular pacing is provided at a programmed rate decoupled from the non-invasive programmed stimulation being delivered in the atrium. Since the ventricular contraction is largely responsible for the total cardiac output, maintaining ventricular contraction during atrial non-invasive programmed stimulation is beneficial and safer for the patient.

Thus, one feature of the present invention is a software algorithm included in the implantable device that controls the transfer of state machines between a standard stimulation state machine and a non-invasive programmed stimulation state machine during a refractory period.

Another feature of the present invention is separate timing control circuitry that allows separate control of the non-invasive programmed stimulation delivery in an atrial chamber of the heart and simultaneous back-up stimulation delivery in a ventricular chamber of the heart.

Another feature of the present invention is a timing algorithm that causes blanking of the sensing circuits associated with heart chambers not being tested whenever a non-invasive programmed stimulation pulse is delivered in a heart chamber undergoing electrophysiological testing.

Thus, the present invention achieves the following two important goals or features: 1) safe, synchronous transfer between a standard stimulation operating mode and a non-invasive programmed stimulation operating mode; and 2) safe decoupling of the device operation delivering stimulation pulses in a heart chamber undergoing electrophysiological testing from the device sensing and stimulation in other heart chambers.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated earlier, the present invention relates to a method for safely implementing non-invasive programmed stimulation (also referred to herein as "NIPS") in an implantable cardiac stimulation device for electrophysiological testing. Operational methods included in the present invention will be described in conjunction with FIGS. 3 through 8. The present invention is intended for use in dual chamber, or multi-chamber cardiac stimulation devices but may also be used in single-chamber devices. The methods of the present invention may be implemented in numerous cardiac stimulation devices capable of delivering electrical stimulation therapy to the heart including pacing, cardioversion, and/or defibrillation. One such device will now be described in conjunction with FIGS. 1 and 2.

Figure 1:
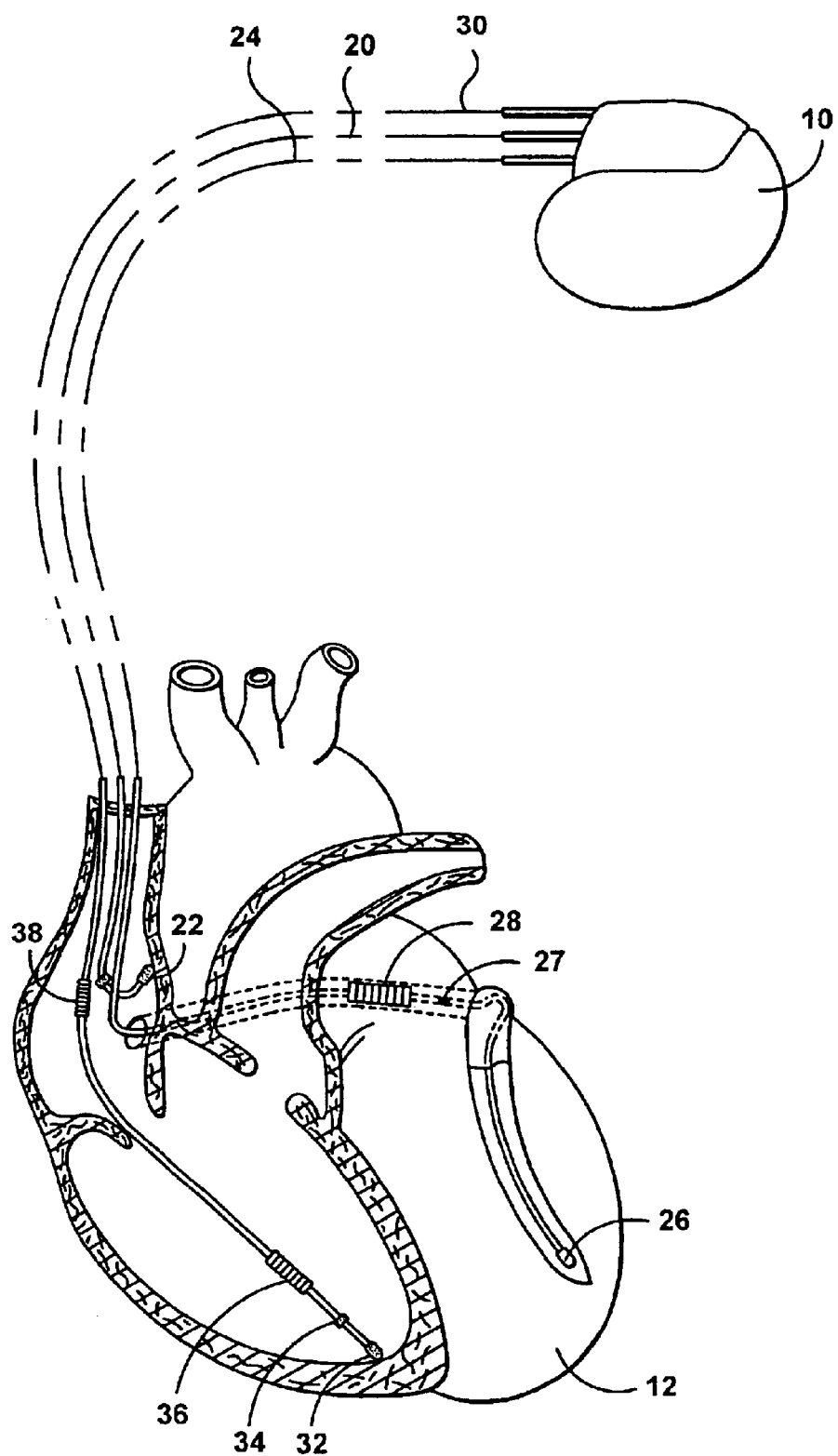
FIG. 1 is a simplified, partly cutaway view illustrating an implantable stimulation device in electrical communication with at least three leads implanted into a patients heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a more detailed description of a coronary sinus lead, refer to U.S. patent application Ser.

No. 09/457,277, titled "A Self-Anchoring, Steerable Coronary Sinus Lead" (Pianca et al.) now abandoned, and U.S. Pat. No. 5,466,254, titled "Coronary Sinus Lead with Atrial Sensing Capability" (Helland), that are incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
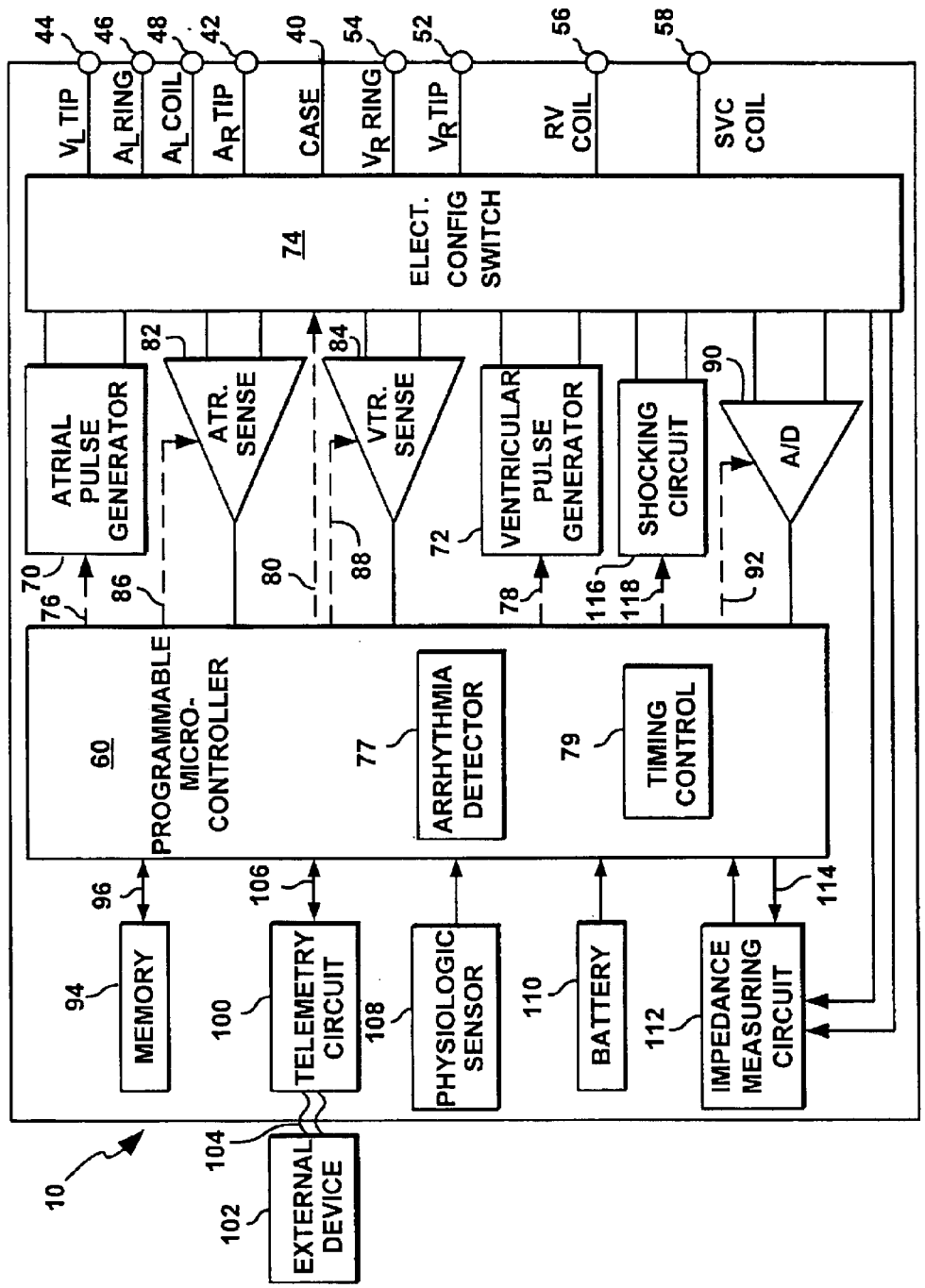
FIG. 2 is a functional block diagram of the multi-chamber implantable stimulation device of FIG. 1, illustrating the basic elements that provide cardioversion, defibrillation and pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals).

As such, in the embodiment of FIG. 2, the connector includes at least a right atrial tip terminal 42 adapted for connection to the atrial (AR) tip electrode 22 in order to achieve right atrial sensing and pacing. To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial ring electrode 27, and the left atrial coil electrode 28, respectively.

To support right ventricular sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively. Thus, the embodiment of FIG. 1 includes one connection port for the right atrial lead 20 and two bipolar, high-voltage connection ports for the right ventricular lead 30 and the coronary sinus lead 24, allowing sensing and stimulation in all four chambers of the heart.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. In accordance with the present invention, software code for transferring between state machines is stored in microcontroller 60. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc. Timing control circuitry 79 preferably includes more than one timer for performing more than one timing event simultaneously. One feature of the present invention is that one timer in the timing control circuitry 79 is used to time events related to the non-invasive programmed stimulation in an atrial chamber of the heart and a separate timer is used simultaneously to time events related to back-up stimulation in a ventricular heart chamber.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity. The sensing circuits 82 and 84 are also referred to as discriminators.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84. For example, in accordance with the present invention, blanking signals are received by sensing circuits associated with heart chambers not undergoing electrophysiological testing whenever stimulation pulses are delivered in the heart chamber that is undergoing electrophysiological testing.

For arrhythmia detection, the stimulation device 10 includes an arrhythmia detector 77 (FIG. 2) that utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired an electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

A feature of the present invention is the ability to send a programming command using the external device 102 to the implanted device 10, in order to request a non-invasive programmed stimulation session for testing arrhythmia induction or termination. This command includes various operating parameters, as will be described in greater detail below, that are used by the non-invasive programmed stimulation state machine in delivering non-invasive programmed stimulation as well as delivering back-up stimulation in other heart chambers upon request.

In one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses. An exemplary physiologic sensor 108 is a minute ventilation sensor.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

As further shown in FIG. 2, the stimulation device 10 is shown as having an impedance measuring circuit 112 which is enabled by the microcontroller 60 by a control signal 114.

When it is a primary function of the stimulation device 10 to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil in electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
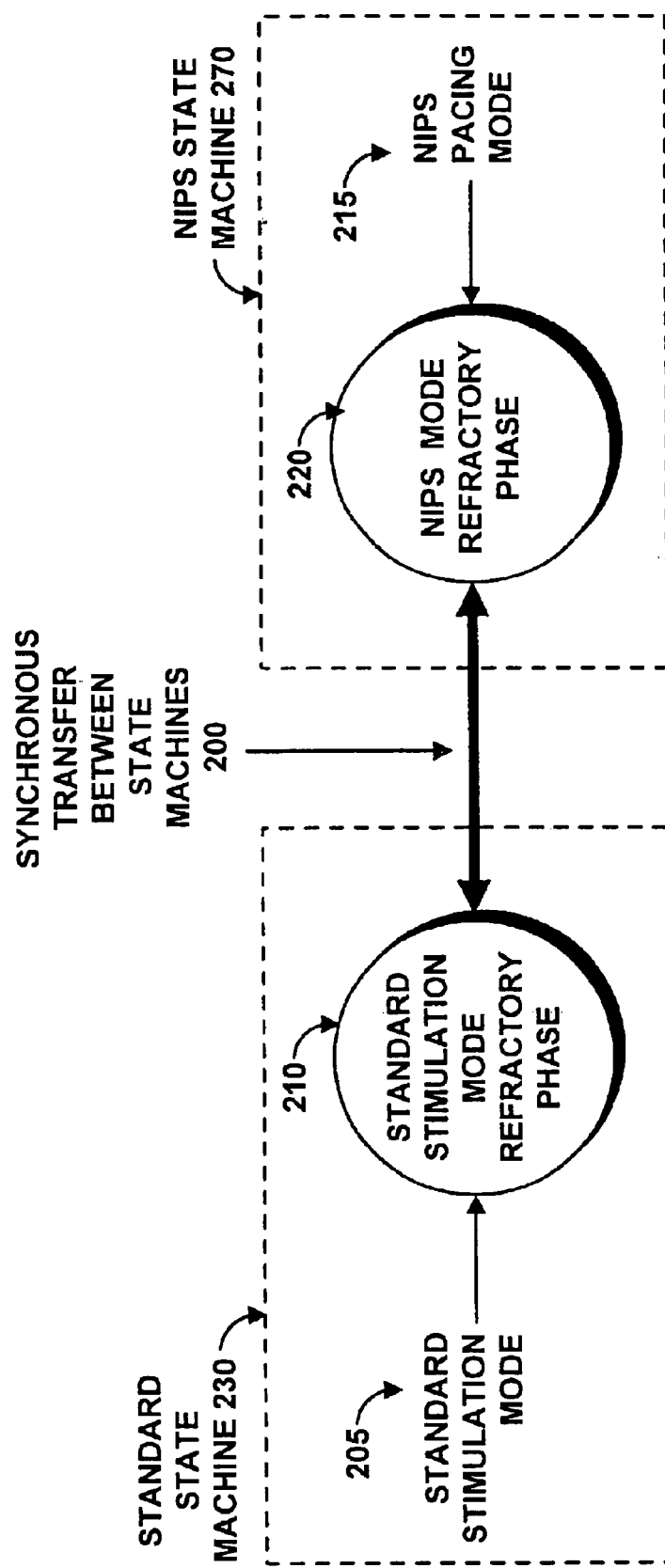
FIG. 3 is an illustration providing an overview of a state machine transfer incorporated in the stimulation device of FIGS. 1 and 2, to allow safe, synchronized switching between standard stimulation operation and non-invasive programmed stimulation for electrophysiological testing.

FIG. 3 depicts an overview of the transition between state machines within the stimulation device 10 for safely transferring from a standard operating mode to a non-invasive programmed stimulation mode and back again. One objective of the present invention is to avoid asynchronous stimulation by including software code in the implanted device 10 that will control a synchronized transfer between the standard stimulation mode to the non-invasive programmed stimulation mode. This state machine transfer is performed during a refractory period following a depolarization of the cardiac chamber to be tested. Such a depolarization may be associated with an intrinsic cardiac event (a detected P-wave or R-wave) or a stimulation pulse (an A-pulse or V-pulse).

Thus, in FIG. 3, the synchronous transfer between state machines 200 is shown to occur between the standard stimulation state machine 230 and the non-invasive programmed stimulation state machine 270 during a refractory phase. The standard stimulation mode 205 is the normal operating mode of the device 10 as programmed by a medical practitioner, such as DDD, VVI, or otherwise.

If the state machine transfer 200 is occurring from the standard state machine 230 to the non-invasive programmed stimulation state machine 270, the transfer occurs during the refractory phase 210 of the standard stimulation mode 205. If the transfer is occurring from the non-invasive programmed-stimulation state machine 270 back to the standard state machine 230, the transfer occurs during the refractory phase 220 of the non-invasive programmed stimulation (NIPS) mode 215. By synchronizing the state machine transfer 200 to the refractory phase following an intrinsic or stimulated event (in the heart chamber to be tested), upon which new timing intervals in the non-invasive programmed stimulation mode will be started, asynchronous stimulation of the cardiac chambers can be avoided when initiating a non-invasive programmed stimulation session. The methods by which this transfer occurs will now be described in greater detail in conjunction with FIGS. 4 through 10.

Figure 4:
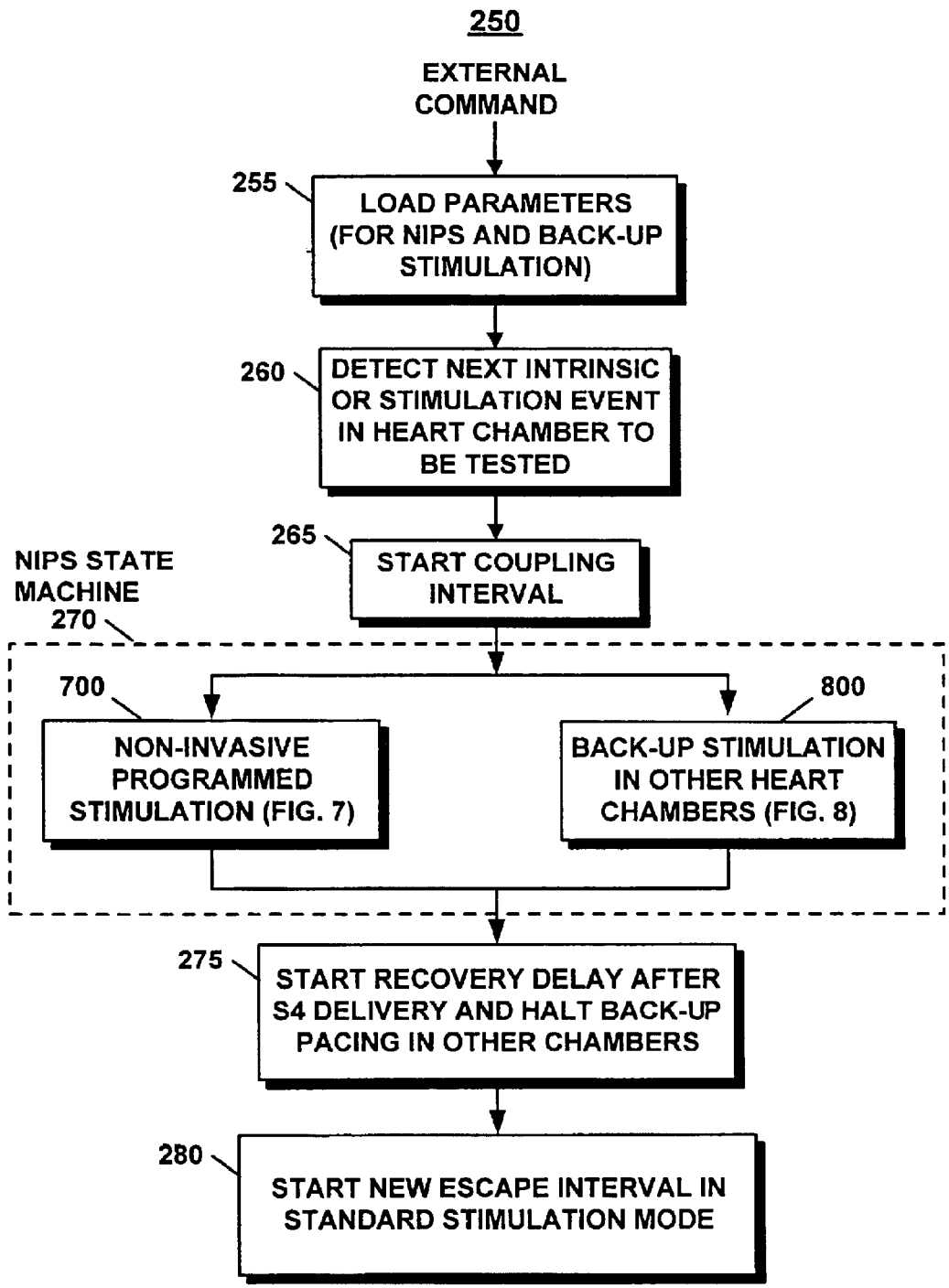
FIG. 4 is a flow diagram providing an overview of a method implemented by the stimulation device of FIGS. 1 and 2, for achieving the state machine transfer illustrated in FIG. 3.

In FIG. 4, a flow chart is shown describing an overview of a method (or algorithm) 250 implemented in one embodiment of the stimulation device 10 for performing the synchronous transfer between the state machines 230, 270 of FIG. 3. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The algorithm 250 begins upon receiving a command from the external programmer 102 operated by a medical practitioner. At step 255, parameter values, as selected by a medical practitioner and received with the external command, are initialized. These parameters will be used by microprocessor 60 in controlling the non-invasive programmed stimulation (NIPS) sequence to be delivered in a heart chamber undergoing electrophysiological testing as well as back-up simulation in other heart chambers if requested. A typical non-invasive programmed stimulation (NIPS) protocol includes a series of high rate pulses, referred to as S1 pulses, followed by one or more, typically three, pulses delivered at progressively increasing rates, referred to as the S2, S3, and S4 pulses.

The pulses S1 through S4 pace the tested heart chamber with the intention of inducing tachycardia or fibrillation. Thus, the operating parameters specified in the external command and loaded at step 255 may include, for example: the heart chamber to be tested, the delay to a first stimulation pulse series S1, the number of pulses to be delivered in the first stimulation pulse series S1, the frequency of these S1 pulses, the coupling interval between the last S1 stimulation pulse and a subsequent S2 pulse, the coupling interval between the S2 pulse and a subsequent S3 pulse, the coupling interval between the S3 pulse and a subsequent S4 pulse, and the back-up stimulation rate to be delivered in non-tested heart chambers.

At step 260, the method 250 waits for the next intrinsic or stimulation event to occur in the heart chamber to be tested. Detection of this event indicates the start of a refractory period in the standard stimulation mode 210 of FIG. 3. During this refractory period, software controls triggered by an interrupt signal generated in response to the detected event are switched from the standard stimulation mode to the non-invasive programmed stimulation mode. For example, a detected P-wave in the atrium will result in an interrupt signal being generated such that microprocessor 60 triggers the execution of software controls in response to the detected P-wave. An "interrupt service routine" would set a timer associated with a base pacing rate or an atrial-ventricular escape interval during the normal stimulation mode. However, if the external command has been received for initiating noninvasive programmed stimulation, the interrupt service routine for transitioning to the non-invasive programmed stimulation state machine is triggered instead.

At step 265, the interrupt service routine starts a timer set to a coupling interval that represents the programmed delay to the first pulse of stimulation series S1. At step 270, the stimulation device 10 begins operating in the non-invasive programmed stimulation state machine. During this operation mode, the stimulation device 10 delivers the non-invasive programmed stimulation in the heart chamber to be tested at step 700 and, if the tested chamber is an atrial chamber, the stimulation device 10 simultaneously delivers a back-up stimulation, if requested, in the ventricle or ventricles at step 800. The method 700 by which the non-invasive programmed stimulation is delivered will be described in greater detail in conjunction with FIG. 7. The method 800 by which back-up stimulation is delivered in a ventricular chamber will be described in greater detail in conjunction with FIG. 8.

After completing the non-invasive programmed stimulation sequence, a recovery delay is started and back-up stimulation is halted at step 275. The stimulation device 10 remains alert to intrinsic events during the recovery delay. The recovery delay allows the sinus node to recover its natural rhythm. During this time, software controls are switched back to the standard stimulation mode such that the interrupt service routine triggered by the last stimulation event transfers the operating mode to the standard state machine.

If an intrinsic event is sensed during the recovery delay, the refractory phase of the non-invasive programmed stimulation mode 220 of FIG. 3 is started after sensing the intrinsic event. However, if no intrinsic event is sensed during the recovery delay, the refractory phase of the non-invasive programmed stimulation mode is started at the end of the recovery delay.

At step 280, a new escape interval is started according to the normal operation of the standard stimulation mode. The stimulation device 10 then carries on according to the pre-existing standard stimulation mode. Detection of any induced arrhythmias may be treated according to programmed parameters in the standard stimulation mode, or may be treated by delivering another non-invasive programmed stimulation command.

Figure 5:
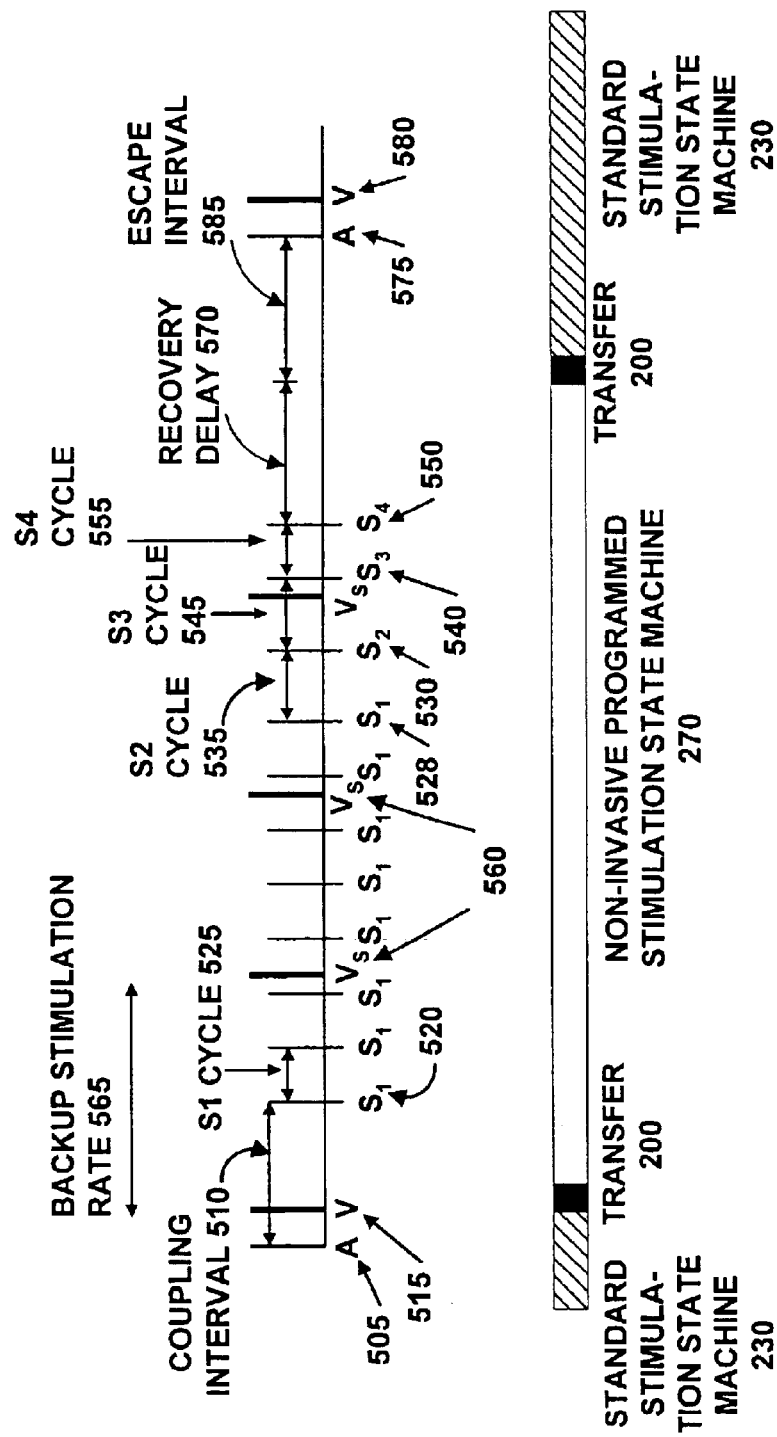
FIG. 5 is a timing diagram depicting a sequence of events occurring during the execution of the method of FIG. 4 for performing atrial non-invasive programmed stimulation triggered by an atrial stimulation pulse.

In FIG. 5, a timing diagram illustrates a sequence of events that may occur during the transfer between state machines according to the algorithm 250 when an atrial non-invasive programmed stimulation command has been received. The atrial stimulation pulse 505 represents the first atrial event occurring during the standard state machine 230 operation after device 10 has received an external command requesting non-invasive programmed stimulation.

A coupling interval 510 is started by an interrupt service routine triggered by the A-pulse event. A ventricular stimulation pulse or V-pulse 515 follows the atrial stimulation pulse 505 at the normal AV interval according to the standard stimulation mode. Thus, the transfer 200 from the standard stimulation state machine 230 to the non-invasive programmed stimulation state machine 270 occurs during the refractory phase immediately following the ventricular stimulation pulse 515.

Upon expiry of the coupling interval 510, the non-invasive programmed stimulation series begins with the delivery of the first S1 pulse 520 according to the programmed parameters. In this example, eight S1 pulses are delivered at a high S1 cycle interval 525, typically at 300 to 400 msec intervals. Following the last S1 pulse 528, an S2 pulse 530 is delivered at the programmed S2 cycle interval 535. Next an S3 pulse 540 is delivered at the programmed S3 cycle interval 545. Finally, an S4 pulse 550 is delivered at the programmed S4 cycle interval 555. Typically these consecutive cycle intervals are progressively decreasing in duration.

As shown in FIG. 5, the atrial non-invasive programmed stimulation is delivered concurrently with ventricular back-up stimulation. Following the last V-pulse 515 in the standard stimulation mode, back-up ventricular stimulation pulses 560 are delivered at the programmed back-up stimulation rate 565. Throughout the non-invasive programmed stimulation, two timers (or a different number of separate timers) within timing control circuit 79 are used to control the timing of the non-invasive programmed stimulation and the back-up stimulation separately. If the timer that controls the non-invasive programmed stimulation and the timer that controls the back-up stimulation expire concurrently, priority is given to the delivery of the non-invasive programmed stimulation pulse. The back-up stimulation pulse is delayed by a predefined amount of time.

Furthermore, throughout the non-invasive programmed stimulation mode, the ventricular sensing circuit 84 is blanked for a pre-defined interval whenever an atrial non-invasive programmed stimulation pulse is delivered. This interval is preferably short in duration, for example 10 to 20 msec. Likewise, if ventricular non-invasive programmed stimulation test is applied, the atrial sensing circuit 82 is blanked whenever a ventricular stimulation pulse is delivered. By providing blanking during the delivery of non-invasive programmed stimulation pulses, inappropriate interpretation of the stimuli as intrinsic events in the non-tested chambers is prevented. In this way, the methods of the present invention provide a safe decoupling of the atrial and ventricular chambers during non-invasive programmed stimulation.

After the last stimulation pulse 550 of the non-invasive programmed stimulation sequence, a recovery delay 570 is started. At the end of this recovery delay 570, the refractory phase of the non-invasive programmed stimulation mode is started, and thus the transfer 200 back to the standard stimulation state machine 230 occurs during this time. At the end of the transfer, a new escape interval 585 is started according to the standard stimulation mode after which a normal atrial stimulation pulse 575 is delivered followed by a ventricular stimulation pulse 580 at the normal AV interval.

Figure 6:
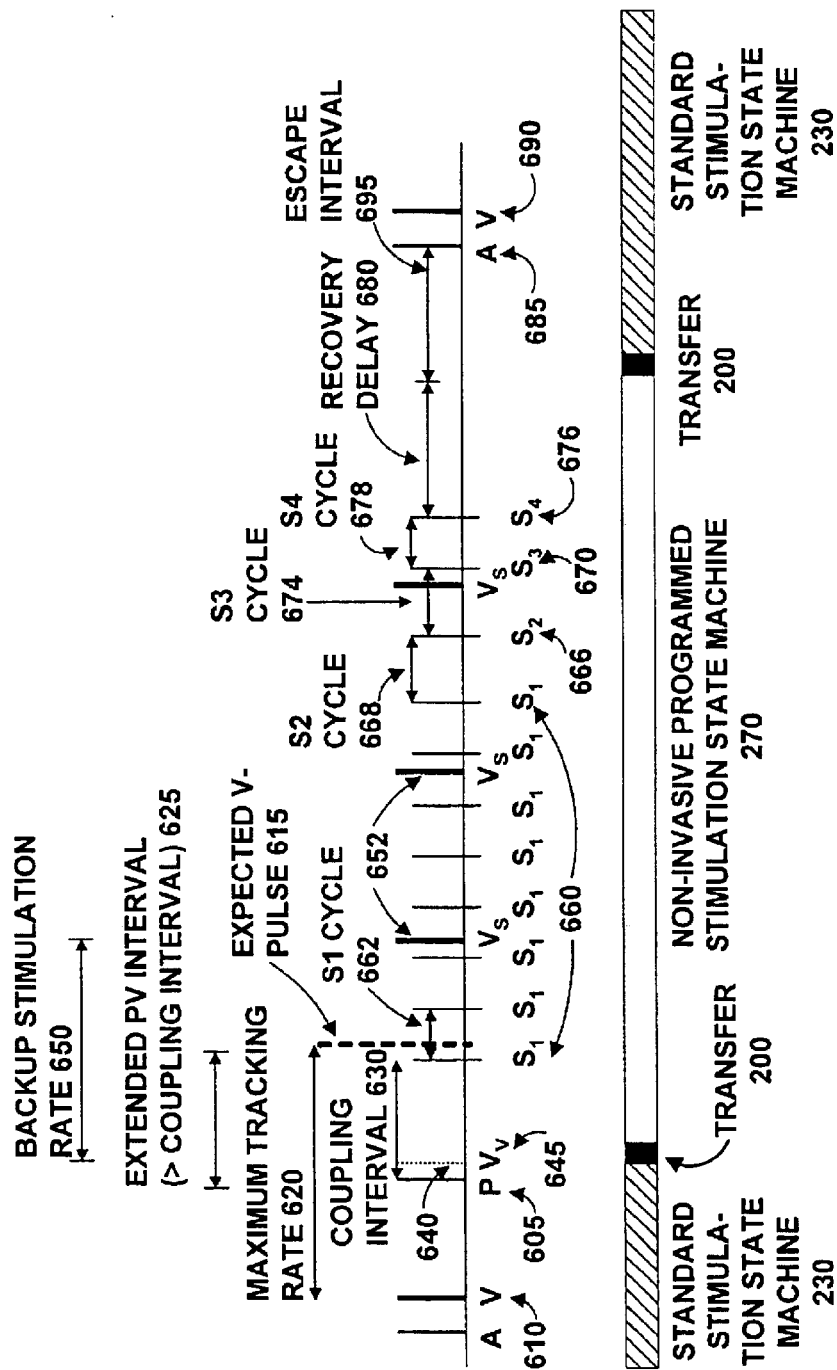
FIG. 6 is a timing diagram depicting a sequence of events occurring during the execution of the method of FIG. 4 for performing atrial non-invasive programmed stimulation triggered by a detected P-wave.

In FIG. 6, a timing diagram illustrates a sequence of events that may occur if, upon receiving the external command to initiate an atrial non-invasive programmed stimulation, the event that triggers the coupling interval is a detected P-wave 605 rather than an A-pulse, as was illustrated in FIG. 5. Normally during the standard stimulation mode, a detected P-wave starts a P-V interval. If this P-V interval expires before detection of an R-wave, then a V-pulse is delivered. However, the time from the most recent ventricular event 610 (V-pulse or detected R-wave) to the expected V-pulse 615 must not be less than a maximum tracking rate 620. This maximum tracking rate 620 normally prevents the ventricular stimulation rate from tracking a high atrial rate. If the programmed P-V interval would cause the next V-pulse to be delivered at a ventricular rate higher than the maximum tracking rate 620, then the P-V interval is automatically extended. The extended P-V interval 625 is such that the next V-pulse 615 is delivered at the maximum tracking rate 620.

However this automatic adjustment of the P-V interval 625 may cause conflict with the transfer to the atrial non-invasive programmed stimulation state machine in that the ventricular pulse may be scheduled to occur after the end of the coupling interval 630. In other words the extended P-V interval 625 triggered during the standard stimulation state 205 is longer than the coupling interval 630 during which the state machine transfer occurs and at the end of which the first pulse of the non-invasive programmed stimulation is delivered. This conflict is to be avoided because the two state machines may not overlap.

The synchronous transfer 200 from the standard stimulation state machine 230 to the non-invasive programmed stimulation state machine 270 must occur during the coupling interval 630 for safe transfer during the refractory phase 210 (FIG. 3). Thus, if an automatic adjustment to the P-V interval is determined necessary during the standard stimulation state machine 230, the software controls initiating the transition to the non-invasive programmed stimulation state machine 270 will perform two actions: 1) re-set the PV interval to a minimum P-V interval setting 640, and 2) inhibit the delivery of the V-pulse. The inhibited V-pulse can be referred to as a "virtual V-pulse" 645. If back-up ventricular stimulation has been requested by the atrial non-invasive programmed stimulation command, V-pulse 652 delivery will begin at the specified back-up stimulation rate 650 after the virtual V-pulse 645.

The non-invasive programmed stimulation sequence is then delivered as programmed beginning upon the expiration of the coupling interval 630. A series of S1 pulses 660, typically eight S1 pulses, are delivered at a programmed S1 cycle interval 662. Following the last S1 pulse, an S2 pulse 666 is delivered at the S2 cycle interval 668. An S3 pulse 670 is delivered at the S3 cycle interval 674, and finally an S4 pulse 676 is delivered at an S3–S4 cycle interval 678. The recovery delay 680 is started after the delivery of the last non-invasive programmed stimulation pulse 676 and the transfer 200 back to the standard stimulation state machine 270 occurs at the end of this time if no intrinsic events are sensed. A new escape interval 695 is initiated after which A-pulses 685 and V-pulses 690 will be delivered according the standard stimulation mode.

Since the noninvasive programmed stimulation may have been intended to induce an arrhythmia, the arrhythmia detection and termination algorithms incorporated in the standard stimulation mode of the implanted device 10 will perform as expected in detecting and terminating the induced arrhythmia. Otherwise, additional non-invasive programmed stimulation commands may be delivered by the medical practitioner to deliver effective anti-arrhythmia therapies. Thus one advantage of the present invention is that the operating code controlling the standard stimulation mode is protected during non-invasive programmed stimulation delivery; the operating code controlling the non-invasive programmed stimulation is executed only when the non-invasive programmed stimulation state machine is enabled.

Figure 7:
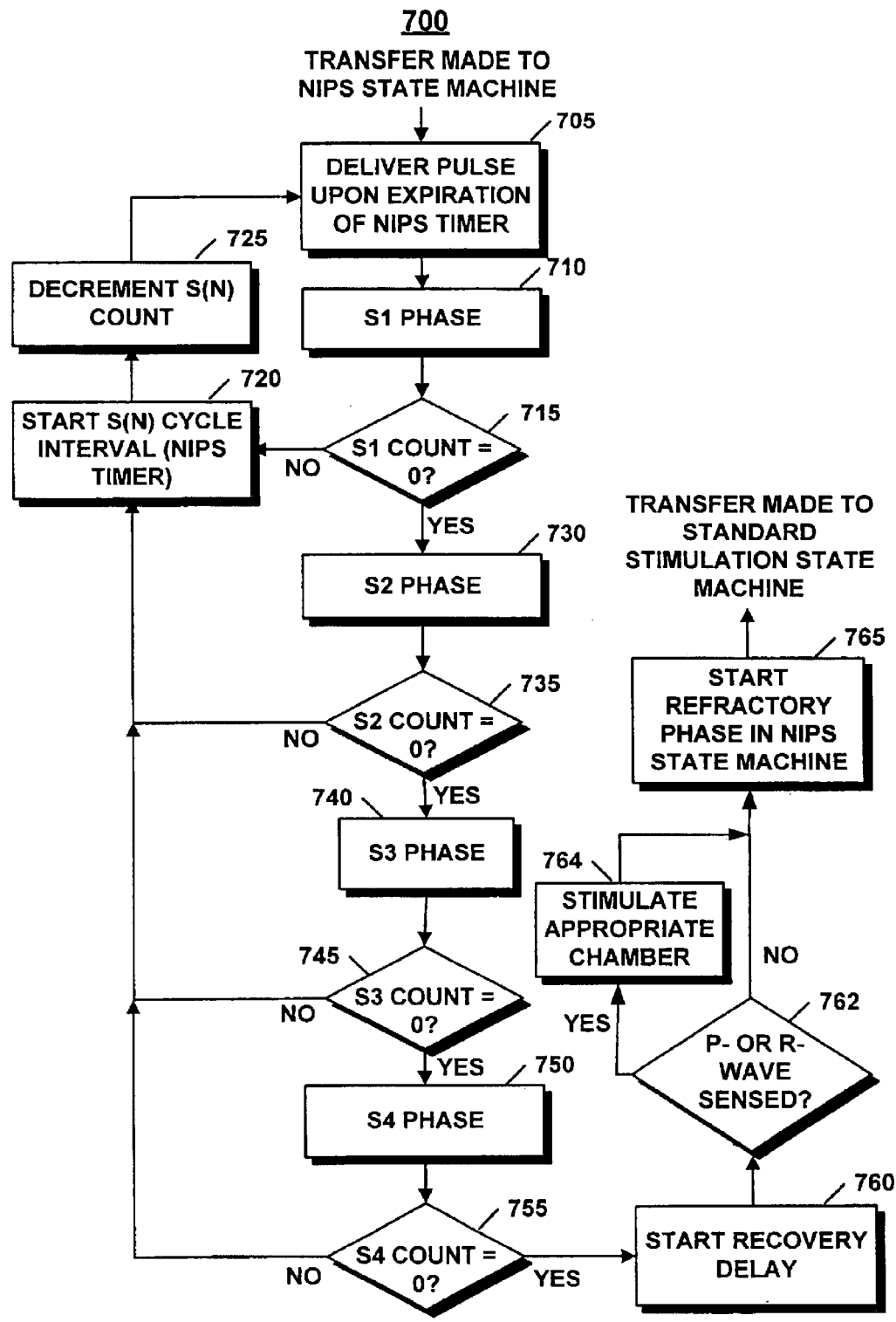
FIG. 7 is a flow diagram of a method implemented by the stimulation device of FIGS. 1 and 2, for performing a non-invasive programmed stimulation sequence in one chamber of the heart.

In FIG. 7, a flow chart is shown depicting an algorithm or method included in one embodiment of the present invention for controlling the delivery of the non-invasive programmed stimulation sequence once the safe transition to the non-invasive programmed stimulation state machine has been made. Beginning at step 705, the first pulse of the non-invasive programmed stimulation is delivered upon the expiration of the non-invasive programmed stimulation (NIPS) timer. The NIPS timer would have been set to the coupling interval 630 during the refractory phase of the standard stimulation mode 210 by the software controls executing the transition from the standard stimulation state machine 230 to the non-invasive programmed stimulation state machine 270.

At step 710, the non-invasive programmed stimulation mode recognizes the S1 phase of the programmed stimulation. The S1 phase has been pre-defined by the external programming command, which includes the number of S1 pulses and the cycle interval of the S1 pulses. Thus a counter keeping track of the number of S1 pulses still to be delivered has been previously set at the programmed number of S1 pulses. At decision step 715, the algorithm 700 determines if the S1 count has reached zero, indicating that all S1 pulses have been delivered. If not, the S1 cycle interval is started by the non-invasive programmed stimulation timer (NIPS timer) at step 720. The S1 count is decremented at step 725, and upon expiration of the NIPS timer, an S1 pulse is delivered at step 705. This process continues until all S1 pulses, typically 8, have been delivered such that the S1 counter is found to equal zero at decision step 715.

The non-invasive programmed stimulation mode then recognizes the S2 phase of the programmed stimulation at step 730. The S2 counter has been previously set equal to the number of S2 pulses to be delivered, typically 1. At step 735, the algorithm 700 determines if the S2 counter has reached zero. If not, the S2 cycle interval is started on the non-invasive programmed stimulation timer (NIPS timer) at step 720, and the S2 count is decremented at step 725. An S2 pulse is then delivered at step 705. Since the S1 count has already reached zero, the algorithm 700 proceeds at decision step 715, and at decision step 735 will now find the S2 counter has reached zero.

Thus, the algorithm 700 proceeds to the S3 phase of the non invasive programmed stimulation at step 750. The S3 count will still be set at the pre-defined number of S3 pulses, typically 1, at decision step 745. Therefore, the S3 cycle interval will be started on the NIPS timer at step 720, and the S3 count will be decremented at step 725. An S3 pulse will be delivered at step 705. At decision steps 715, 735, and 745, the S1, S2, and S3 counters are now all found to be equal to zero, thus algorithm 700 proceeds to the S4 phase at step 750. The S4 count will initially be set equal to the pre-defined number of S4 pulses to be delivered, therefore the S4 cycle interval will be started at step 720, and the S4 count decremented at step 725. Upon expiration of the NIPS timer, an S4 pulse will be delivered at step 705.

Once all counters are found to be equal to zero, the algorithm 700 proceeds to step 760 to start the sinus node recovery delay. At the end of the sinus node recovery delay the algorithm 700 will put the non-invasive programmed stimulation state machine into the refractory phase 220 (FIG. 3) at step 765. During this phase, the safe, synchronous transfer 200 back to the standard stimulation state machine 230 will be made. The algorithm 700 inquires at decision step 762 if a cardiac event has been sensed. If during the sinus node recovery delay an intrinsic event is sensed, the appropriate cardiac chamber is stimulated at 764, and the refractory period is started following the intrinsic event at 765. If, on the other hand, no intrinsic event is sensed during the sinus node recovery delay, the algorithm 700 starts the refractory period at the expiration of the recovery delay, at step 765. Following step 765, the algorithm 700 effects the transfer back to the standard stimulation state machine.

Figure 8:
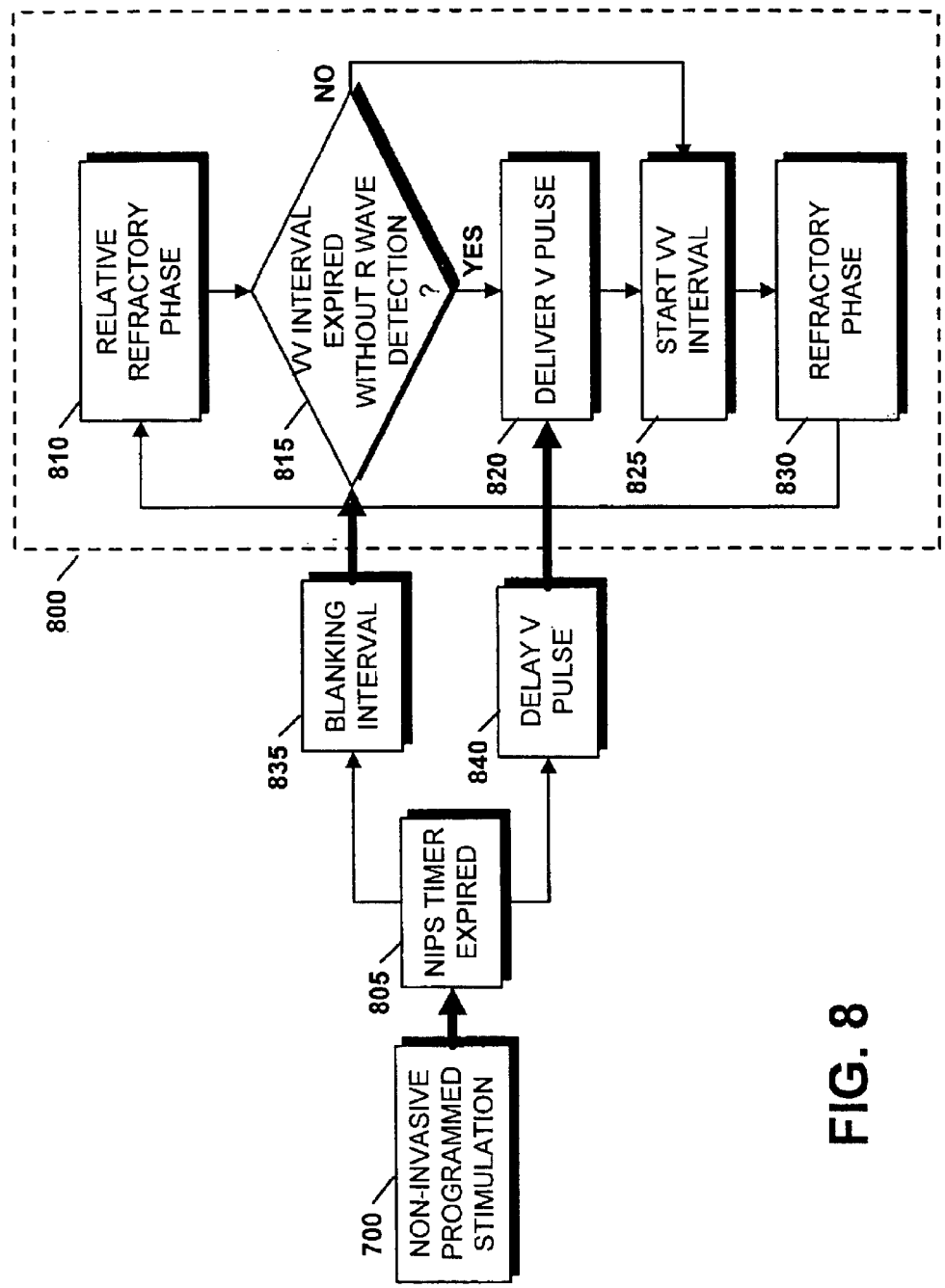
FIG. 8 is a flow diagram of a method implemented by the stimulation device of FIGS. 1 and 2, for performing out ventricular back-up stimulation during atrial non-invasive programmed stimulation.

In FIG. 8, a flow chart is shown depicting an algorithm or method 800 included in one embodiment of the present invention for providing back-up stimulation in the ventricles while performing atrial non-invasive programmed stimulation. The back-up stimulation 800 occurs simultaneously with the atrial non-invasive programmed stimulation 700. Once the non-invasive programmed stimulation state machine 270 has been enabled, the ventricular back-up stimulation begins during the relative refractory phase at step 810. A ventricular back-up stimulation interval (VV interval) will have been initiated upon the last ventricular event occurring before the transfer of state machines or upon a "virtual V" in the case described in conjunction with FIG. 6 above. If an intrinsic R-wave is detected prior to the expiration of the W interval as determined at decision step 815, a new W interval is started at step 825.

However, if the VV interval expires without the detection of an intrinsic R-wave as determined at decision step 815, a ventricular stimulation pulse (V-pulse) is delivered at step 820. A new VV interval will then be started at step 825 as well as the refractory phase at step 830. The back-up stimulation mode 800 is repeated as long as the device 10 remains in the non-invasive programmed stimulation state machine. Thus it is seen that, during atrial non-invasive programmed stimulation, device 10 effectively operates in an AOO pacing mode decoupled from a VVI pacing mode, i.e., triggered single chamber pacing in the atrium decoupled from demand pacing in the ventricle. Alternatively, VOO pacing could be delivered in the ventricle.

Throughout this process, the non-invasive programmed stimulation algorithm 700 notifies the microcontroller 60 whenever the non-invasive programmed stimulation timer (NIPS timer) expires 805. Software controls will then take two actions as necessary: 1) trigger a blanking interval at step 835 to prevent the ventricular sensing circuit 84 from sensing the atrial non-invasive programmed stimulation pulse that is delivered upon expiration of the NIPS timer, or 2) trigger a short delay of the ventricular stimulation pulse at step 840 in the case that the VV interval has expired at the same time as the NIPS timer. The ventricular pulse is delayed in order to avoid simultaneous contraction of the atrium and the ventricle and to avoid a hardware limitation that prevents the time required for the charge pump to build charge into the storage capacitors.

In one embodiment, device 10 may include a physiological sensor 108 which allows the device 10 to be rate responsive to changes in patient activity or metabolic demand. Typically in such devices, processing of commands for changing state machine is only possible following a ventricular event, not an atrial event. When the present invention is incorporated into such devices, software controls overcome this problem when an atrial non-invasive programmed stimulation is requested. The software controls perform the following tasks: 1) detect the atrial event that the coupling interval should be started after, 2) start the coupling interval and force the immediate safe transfer to the non-invasive programmed stimulation state machine, and 3) if ventricular back-up pacing is requested, start the VV interval for back-up stimulation at the most recent ventricular event. In this way the transfer of state machines is done by imposing a synchronous state after the atrial triggering event so that the transfer does not have to be delayed until the next ventricular event.

Figure 9:
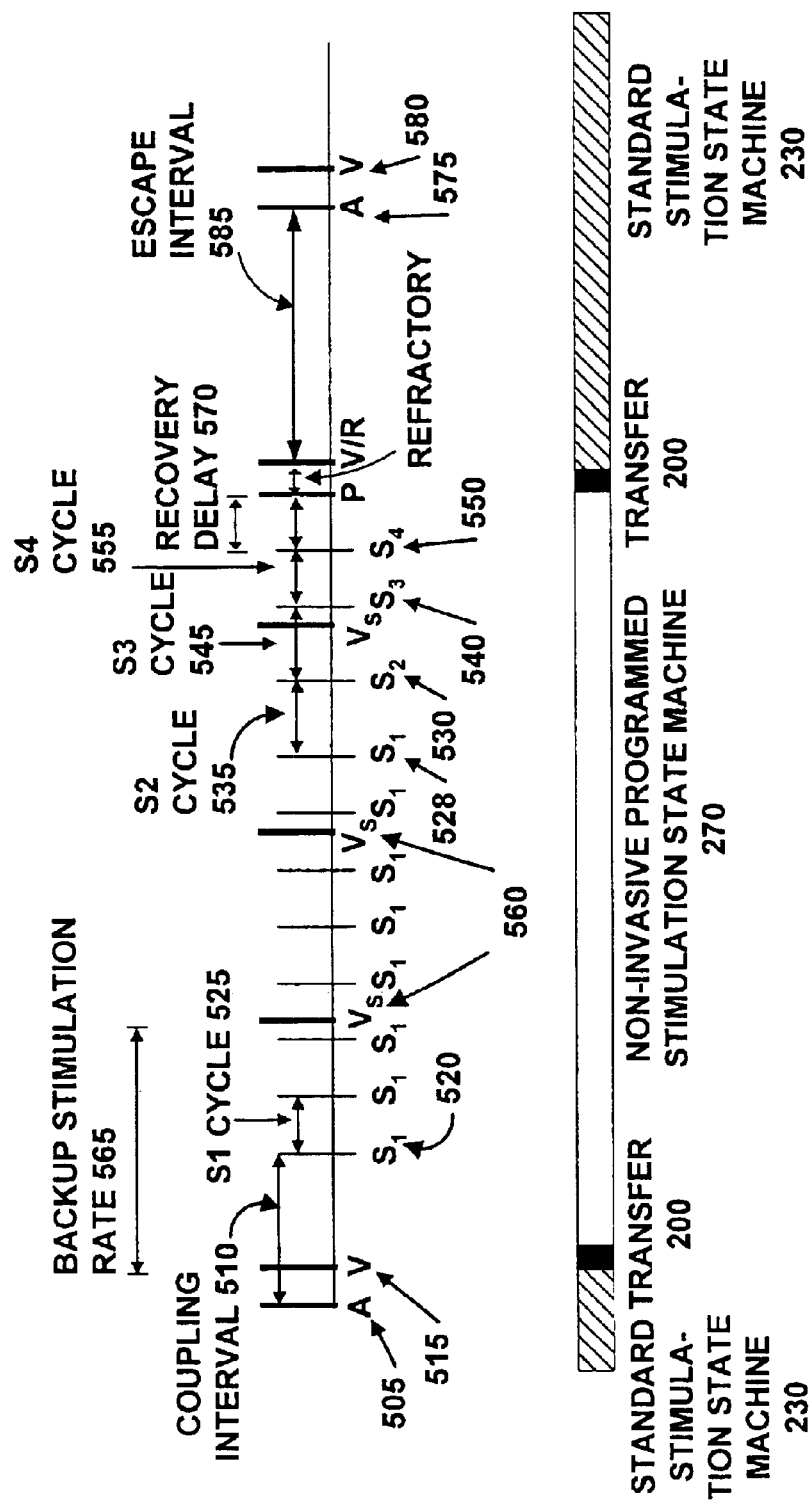
FIG. 9 is a timing diagram depicting a sequence of events occurring during the execution of the method of FIG. 4 for performing atrial non-invasive programmed stimulation triggered by an atrial stimulation pulse, with an intrinsic activity sensed during a recovery delay.
Figure 10:
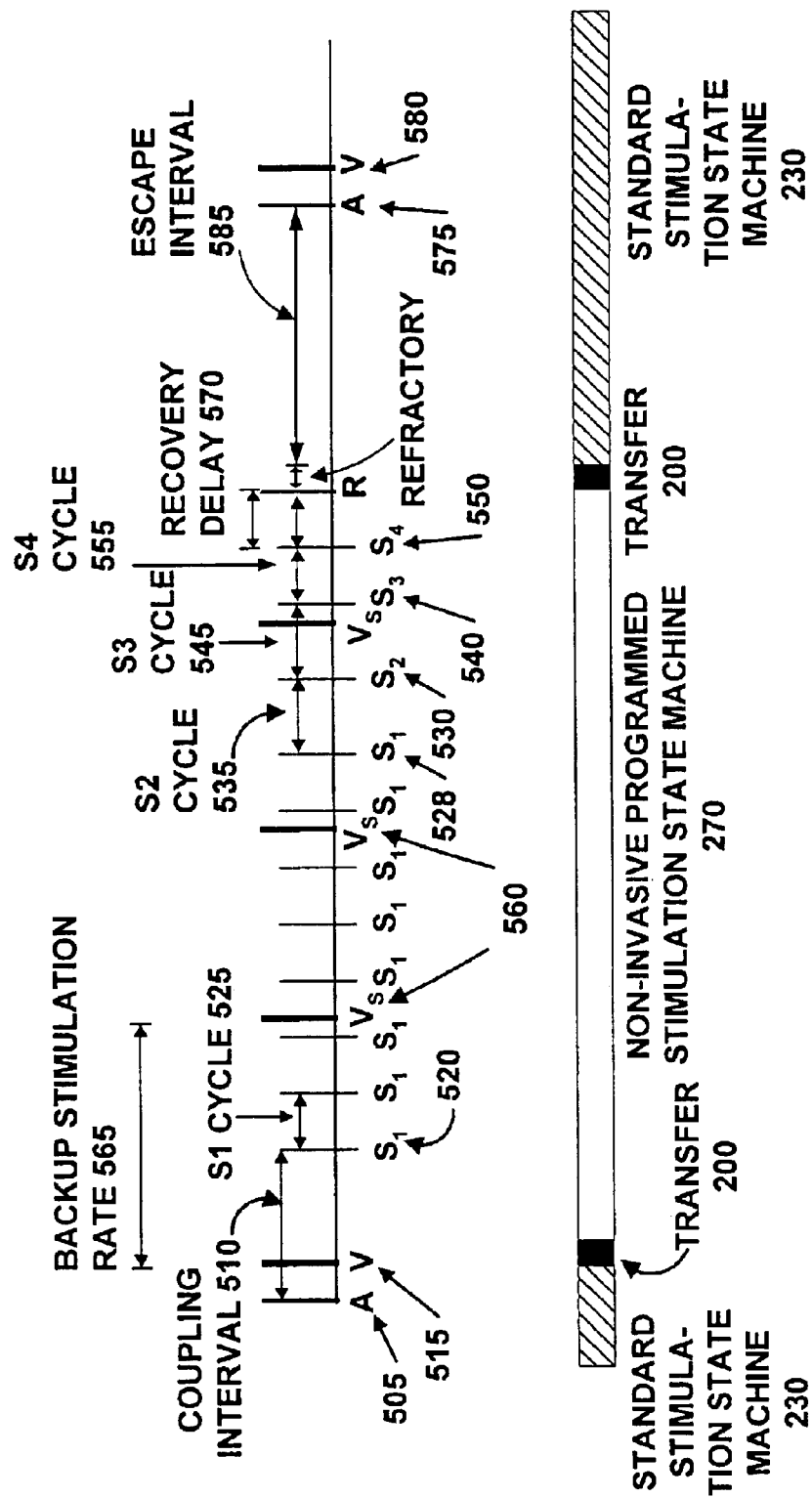
FIG. 10 is a timing diagram depicting a sequence of events occurring during the execution of the method of FIG. 4 for performing atrial non-invasive programmed stimulation triggered by a detected P-wave, with an intrinsic event sensed during the recovery delay.

FIGS. 9 and 10 are substantially similar to FIGS. 5 and 6, respectively, except that in FIGS. 9 and 10, an intrinsic event, such as a P-wave or an R-wave, that occurs during the recovery delay 570.

Thus, a method has been described that achieves safe, cardiac-synchronized transfer between a standard stimulation state machine of an implantable device to a non-invasive programmed stimulation state machine. Using the present invention, non-invasive electrophysiological testing using an implanted cardiac stimulation device can be safely performed in either the atria or the ventricles, depending on the system implanted, with sensing and stimulation in the non-tested chambers safely decoupled from the non-invasive programmed stimulation in the tested chamber. The transfer of pacing state machines can be used for antitachycardia therapy; in that if a tachycardia condition is confirmed, the stimulation device transfers from the standard stimulation state machine to the non-invasive programmed stimulation state machine.

An important advantage of the present invention over existing technology is that asynchronous stimulation at the onset of a non-invasive programmed stimulation protocol is avoided. Further, during atrial electrophysiological testing, back-up stimulation in the ventricle is possible. While the invention herein disclosed has been described according to specific embodiments and applications thereof, numerous modifications and variations could be made thereto by those skilled in the art without departing from the scope of the invention.

What is claimed is:

1. A stimulation device capable of performing electrophysiological testing by delivering non-invasive programmed stimulation, comprising:
   a discriminator that senses a cardiac event in a cardiac chamber being tested;
   timing circuitry, coupled to the discriminator, that triggers an onset of the non-invasive programmed stimulation based on a detected cardiac event occurring in the cardiac chamber being tested;
   a controller, connected to the timing circuitry that executes a transfer between a first and a second stimulation mode; and
   an energy generator connected to the discriminator, the timing circuitry and the controller, the generator is controlled by the controller to deliver a sequence of stimulation pulses to the cardiac chamber being tested in response to the detected cardiac event.

2. The stimulation device of claim 1, wherein the timing circuitry sets a refractory period that follows a triggering detected cardiac event; and
   wherein the controller executes the transfer during the refractory period.

3. The stimulation device of claim 2, wherein the controller executes the transfer between the first and the second stimulation mode by switching from a standard operating mode to a non-invasive programmed stimulation mode.

4. The stimulation device of claim 3, further including a programmer that generates an external command; and
   wherein the timing circuitry triggers the onset of the non-invasive programmed stimulation in response to the external command.

5. The stimulation device of claim 3, wherein the discriminator detects any one of an atrial intrinsic event, venticular intrinsic event, an atrial stimulated event, or a ventricular stimulated event in the cardiac chamber being tested.

6. The stimulation device of claim 3, wherein the timing circuitry further sets a recovery delay at the expiration of the non-Invasive programmed stimulation.

7. The stimulation device of claim 6, wherein the timing circuitry is operative to start a second refractory period following the expiration of the recovery delay if no intrinsic event is detected during the recovery delay.

8. The stimulation device of claim 7, wherein the controller further effects a transfer from the non-invasive programmed stimulation mode to the standard operating mode during the second refractory period.

9. The stimulation device of claim 1, wherein the energy generator further provides backup ventricular stimulation whenever atrial non-invasive programmed stimulation is performed.

10. The stimulation device of claim 9, wherein the energy generator provides back-up ventricular stimulation at a programmed rate that is decoupled from the atrial non-invasive programmed stimulation.

11. A stimulation device capable of performing electrophysiological testing by delivering non-invasive programmed stimulation, comprising:
    a sensing circuitry to detect a cardiac event in a cardiac chamber to be tested;
    a controller coupled to the sensing circuitry, the controller to implement an electrophysiological testing scheme in response to detection of the cardiac event; and
    a pulse generator coupled to the controller, the pulse generator to deliver a sequence of stimulation pulses to the cardiac chamber as dictated by the testing scheme;

wherein the controller comprises a timing control circuitry coupled to the sensing circuitry, the timing control circuitry to trigger an onset of the non-invasive programmed stimulation based on the detected cardiac event occurring in the cardiac chamber being tested; and wherein the controller implements the testing scheme during a refractory period.

12. The stimulation device of claim 11, wherein the electrophysiological testing scheme comprise a transfer from a standard operating mode to a non-invasive programmed stimulation mode.

13. The stimulation device of claim 12, wherein the sensing circuitry detects any one of an atrial intrinsic event, ventricular intrinsic event, an atrial stimulated event, or a ventricular stimulated event in the cardiac chamber being tested.

14. The stimulation device of claim 12, wherein the timing control circuitry further sets a recovery delay at the expiration of the non-invasive programmed stimulation.

15. The stimulation device of claim 14, wherein the timing control circuitry is operative to start a second refractory period following the expiration of the recovery delay if no intrinsic event is sensed during the recovery delay.

16. The stimulation device of claim 15, wherein the controller further effects a transfer from the non-Invasive programmed stimulation mode to the standard operating mode during the second refractory period.

17. The stimulation device of claim 11, wherein the pulse generator further provides back-up venticular stimulation whenever atrial non-invasive programmed stimulation is performed.

18. The stimulation device of claim 17, wherein the pulse generator provides back-up ventricular stimulation at a programmed rate that is decoupled from the atrial non-invasive programmed stimulation.

19. The stimulation device of claim 11, wherein the controller further effects a transfer from the test mode to a normal mode if a failure occurs during the non-invasive programmed stimulation.

* * * * *